(12) United States Patent
Nakai et al.

(10) Patent No.: US 9,574,213 B2
(45) Date of Patent: Feb. 21, 2017

(54) METHOD OF ORGANIC ACID FERMENTATION BY RUMEN FLUID USING CELLULOSE-CONTAINING WASTE MATTER

(75) Inventors: Yutaka Nakai, Sendai (JP); Yasunori Baba, Sendai (JP); Chika Tada, Sendai (JP); Yasuhiro Fukuda, Sendai (JP)

(73) Assignee: TOHOKU UNIVERSITY, Sendai-Shi, Miyagi (JP)

( * ) Notice: Subject to any disclaimer, the term of this patent is extended or adjusted under 35 U.S.C. 154(b) by 0 days.

(21) Appl. No.: 13/878,469

(22) PCT Filed: Oct. 21, 2011

(86) PCT No.: PCT/JP2011/074277
§ 371 (c)(1),
(2), (4) Date: May 24, 2013

(87) PCT Pub. No.: WO2012/053631
PCT Pub. Date: Apr. 26, 2012

(65) Prior Publication Data
US 2013/0236939 A1   Sep. 12, 2013

(30) Foreign Application Priority Data
Oct. 22, 2010 (JP) .................. 2010-237676

(51) Int. Cl.
| | | |
|---|---|---|
| *C12P 7/54* | (2006.01) | |
| *C12N 1/22* | (2006.01) | |
| *C12P 7/52* | (2006.01) | |
| *C02F 3/00* | (2006.01) | |
| *C12P 5/02* | (2006.01) | |
| *D21C 5/02* | (2006.01) | |

(52) U.S. Cl.
CPC .. *C12P 7/54* (2013.01); *C02F 3/00* (2013.01); *C12N 1/22* (2013.01); *C12P 5/023* (2013.01); *C12P 7/52* (2013.01); *D21C 5/02* (2013.01); *C12P 2203/00* (2013.01); *Y02E 50/343* (2013.01); *Y02W 30/648* (2015.05)

(58) Field of Classification Search
CPC .................................. C12P 7/54; C12P 5/023
USPC ................................................. 435/140, 167
See application file for complete search history.

(56) References Cited

U.S. PATENT DOCUMENTS

| | | |
|---|---|---|
| 5,648,258 A | 7/1997 | Odom |
| 2009/0137016 A1* | 5/2009 | Kohn ............................ 435/160 |

FOREIGN PATENT DOCUMENTS

| | | |
|---|---|---|
| JP | 10-229889 | 9/1998 |
| JP | 2000-232892 | 8/2000 |
| JP | 2002-176997 | 6/2002 |
| JP | 2002-186938 | 7/2002 |
| JP | 2007-202518 | 8/2007 |
| WO | 2009024294 A1 | 2/2009 |

OTHER PUBLICATIONS

Hobson PN. Continuous Culture of Some Anaerobic and Facultatively Anaerobic Rumen Bacteria. 1965. J. Gen. Microbiol. 38, 167-180.*
International Search Report of International Application No. PCT/JP2011/074277 mailed Dec. 6, 2011.
International Preliminary Report on Patentability of International Application No. PCT/JP2011/074277 mailed Apr. 25, 2013.
Van Gylswyk, N. O. et al., "Comparative growth rates of various rumen bacteria in clarified rumen fluid from cows and sheep fed different diets", Applied and Environmental Microbiology, Jan. 1992, vol. 58, No. 1, pp. 99-105.
Gijzen, H. J. et al., "Application of rumen microorganisms for an enhanced anaerobic degradation of solid organic waste materials" Biological Wastes vol. 22, Issue 2, 1987, pp. 81-95.
Koike, S., "Rumen ni Kakusareta Miryoku II) Ushi o Sasaeru Micro na Tateyakusha Rumen Saikin" Livestock Technology, Oct. 1, 2010, No. 665, pp. 7-11.
Slyter, L. L. et al., "Sulfur influences on rumen microorganisms in vitro and in sheep and calves", Journal of Animal Science, 1986, vol. 63(6), pp. 1949-1959.
McSweeney, C. S. et al., "Effect of sulfur supplements on cellulolytic rumen micro-organisms and microbial protein synthesis in cattle fed a high fibre diet", Journal of Applied Microbiology, Nov. 2007, vol. 103, Issue 5, pp. 1757-1765.
Kobayashi, Y., "Rumen ni Kakusareta Miryoku I) Rumen ni Kakusareta Miryoku Chikusan, Kankyo, Sonota no Sangyo eno Oyo Tenkai", Livestock Technology, Oct. 1, 2010, No. 665, pp. 2-7.
Zikakis, J. P. et al., "Metabolism of Sulfur Amino Acids by Rumen Microorganisms", Journal of Dairy Science, vol. 52, Issue 12, Dec. 1969, pp. 2014-2019.
Kivaisi, A. K., et al., "Application of rumen microorganisms for enhanced anaerobic degradation of bagasse and maize bran", Biomass and Bioenergy, 1995, vol. 8, No. 1, pp. 45-50.
Xiaohua, et al., "Effect of Inorganic salton the aceticlastic methanogensmethane fermentation kinetics", Transactions of the CSAE, vol. 22, Supp 2, pp. 5-9, (Dec. 31, 2006).

(Continued)

*Primary Examiner* — Paul Holland
(74) *Attorney, Agent, or Firm* — Ping Wang; Andrews Kurth Kenyon LLP (57) ABSTRACT

The present application provides a method for producing organic acid, such as acetic acid, propionic acid, butyric acid, or another high-quality raw material designed for methane fermentation and obtained by converting waste paper and other forms of cellulose-based biomass to organic acid, wherein said method comprising a step for reacting rumen fluid collected from a ruminant animal with cellulose-containing waste matter. This method provides the effective use of cellulose-containing waste matter, which is a high-quality fermentation resource.

21 Claims, 7 Drawing Sheets

(56) References Cited

OTHER PUBLICATIONS

Extended European Search Report of International Application No. PCT/JP2011/074277 mailed Mar. 31, 2016.
Mourino, F. et al., "Initial pH as a determinant of cellulose digestion rate by mixed ruminal microorganisms in vitro", J. Dairy Sci., Apr. 2001, vol. 84(4), pp. 848-859.
Gijzen, H. J. et al., "Application of rumen microorganisms for an enhanced anaerobic degradation of solid organic waste materials", Biological Wastes, 1987, vol. 22(2), pp. 81-95. (Abstract only).

* cited by examiner

METHOD OF ORGANIC ACID FERMENTATION BY RUMEN FLUID USING CELLULOSE-CONTAINING WASTE MATTER

This application is a National Stage Application of PCT/JP2011/074277, filed Oct. 21, 2011, which claims priority from Japanese Patent Application No. 2010-237676, filed Oct. 22, 2010. The entirety of all of the aforementioned applications is incorporated herein by reference.

FIELD

The present invention is related to a method for the production of organic acids such as acetic acid and propionic acid to serve as a raw material for methane fermentation and for other useful compounds, comprising reacting rumen fluid collected from a ruminant such as cattle with cellulose-containing waste.

BACKGROUND OF THE INVENTION

Used paper in an office such as classified papers is currently subjected to a finely cutting treatment. As a certain level of strength needs to be maintained during the production of recycle paper from waste paper, its recycling number has to be limited and all of the waste paper recovered is not suitable for recycling.

In the past, cellulose-containing waste such as the finely-cut office paper and a kind of waste paper that is not suitable for recycling have been mostly incinerated and not been therefore effectively utilized. Incineration leads to energy loss, and will produce a huge amount of greenhouse gas, carbon dioxide. There is a necessity of a method for utilizing the waste paper that is hard to recycle.

Recently, techniques have been reported for the production of ethanol with fermentation of glycosylated products of the cellulose-containing waste by an enzyme such as cellulase (Patent Documents 1 and 2), or an acid (Patent Document 3).

PRIOR ARTS

Patent Documents

Patent Document 1: Japanese Patent Publication 2002-176997
Patent Document 2: Japanese Patent Publication 2002-186938
Patent Document 3: Japanese Patent Publication 2007-202518

Problem to be Solved by the Invention

The above methods of glycosylation with the enzyme and the acid treatment in the prior arts have an advantage of a relatively fast treatment rate. However, the enzyme (cellulase) is expensive, and a method for recovering and re-utilizing of said enzyme has not yet established. There is another problem that said enzyme can not decompose lignin that will prohibit glycosylation. On the other hand, the acid treatment is not preferable from an environmental point of view, and the neutralization of the waste water is therefore necessary in the acid treatment. Furthermore, a bone structure of sugars itself will be partly destroyed due to the over-decomposition with the acid. Accordingly, the above methods with the enzyme and the acid in the prior arts have problems such as a high cost, a high environmental burden and a low efficiency.

Since the cellulose-containing waste is cellulose-based biomass that is a high-quality material for fermentation, an effective method for its utiliation has been desired.

Means for Solving the Problems

The present inventors have studied hard to solve the above problems, and found that organic acids to serve as a substrate for methane fermentation, especially, acetic acid that is most accessible to methane bacteria will be obtained as a main decomposed matter when the waste paper is soaked in raw rumen fluid. The present invention is based on the above findings.

The present invention is therefore related to the following aspects:

[1] A method for the production of organic acids to serve as a raw material for methane fermentation, comprising reacting rumen fluid collected from a ruminant with cellulose-containing waste.

[2] The method according to Aspect 1, wherein the cellulose-containing waste is waste paper.

[3] The method according to Aspect 1 or 2, wherein the ruminant is cattle.

[4] The method according to any one of Aspects 1-3, wherein the reaction between the rumen fluid collected from the ruminant with the cellulose-containing waste is carried out in anaerobic conditions.

[5] The method according to Aspect 4, wherein the anaerobic conditions are generated by co-existence of a compound with a reducing property selected from the group consisting of cysteine, sodium sulfate, ascorbic acid, methionine, thioglycolic acid, DDT and any combination thereof in a system of the reaction between the rumen fluid collected from the ruminant with the cellulose-containing waste.

[6] The method according to Aspect 5, wherein a cysteine concentration in the reaction system is 0.025~0.25% by weight.

[7] The method according to Aspect 5, wherein the reaction between the rumen fluid with the cellulose-containing waste is carried out in a closed system under atmosphere of nitrogen or hydrogen.

[8] The method according to any one of Aspects 4~7, wherein the reaction is kept at 30° C.~45° C.

[9] The method according to any one of Aspects 4~8, wherein pH of the reaction is in a range of 5.0~8.0.

[10] The method according to any one of Aspects 1~9, wherein a waste concentration in the reaction system is 0.5%~7% by weight.

[11] The method according to any one of Aspects 1~10, wherein a final concentration of generated acetic acid is 10 g/L (reaction mixture) or more.

[12] A method for the production of methane, comprising performing methane fermentation using as a raw material the organic acids or processed rumen fluid containing the organic acids produced by the method according to any one of Aspects 1~11.

Advantages of the Invention

According to the method of the present invention, the cellulose-based biomass such as the waste paper could be converted into the organic acids to give a high-quality raw material for methane fermentation such as acetic acid, propionic acid and butyric acid. The above method could shorten a reaction time required for the production of the raw material for methane fermentation (acceleration of the acid fermentation) and significantly increase an amount of the production of acetic acid that is a main final-product for the raw material for methane fermentation. Methane could be produced effectively by using the organic acids such as acetic acid or processed rumen fluid containing the organic acids thus produced.

The present invention has the following excellent advantages over the prior arts: It is of a low-cost since it can utilize waste rumen fluid of butchered livestock; its environmental burden is low since the processed fluid can be directly subjected to methane fermentation without any treatment for waste liquid; it will promote the glycosylation of the waste paper since the rumen fluid contains microorganisms that will break an ether bond, a main bond of lignin; and it will not induce the destruction of the bone structure of sugar since the treatment with the microorganisms is mild.

BEST MODE FOR CARRYING OUT THE INVENTION

The present invention relates to a method for the production of organic acids to serve as the raw material for methane fermentation such as acetic acid, propionic acid and butyric acid, comprising reacting the rumen fluid collected from a ruminant with the cellulose-containing waste.

The term "cellulose-containing waste" means any waste material that has been generated as a result of industrial activities and daily consumption activities, including those containing cellulose as a main component. Its origin and kind are not limited. A representative of the cellulose-containing waste is the waste paper such as the used paper in the office. The above waste may be optionally subjected to pre-treatment such as fracturing, crushing or cutting depending on its shape, conditions and the like before it is reacted with the rumen fluid.

The "rumen" is present in the ruminant such as cattle in order to utilize the fiber of plants as energy source. In the case of the cattle, it forms a gigantic bursa (first stomach) that occupies almost all part in the left side and half a part (a rear part) in the right side of its abdominal cavity. The rumen occupies 80% of the whole of a multiple stomach consisting of the first to forth stomach, and has become about 200 liter (L) in volume in an adult cow. A lot of feed will be stored in the rumen and decomposed by microorganisms living therein. About 90% of the rumen content consists of water so that fermentation will be sufficiently performed with the microorganisms.

An infinite number of bacteria are living in the rumen, which include about $10^9 \sim 10^{11}$ bacteria with 60 kinds or more (cellulolytic bacteria, amylolytic bacteria, proteolytic bacteria, etc.) per 1 g of the rumen content and about $10^5 \sim 10^6$ protozoa with 90 kinds or more per 1 g of the rumen content. The decomposition of the feed and synthesis are actively carried out by these microorganisms in the rumen.

The "rumen fluid" used in the present invention is an aqueous solution (fluid in the first stomach) containing various kinds of the microorganisms living in the rumen of the ruminant, and will be about 200 L per an individual of the cattle. The rumen fluid can be easily collected from the rumen of the ruminant by any method known for those skilled in the art. The rumen fluid that is collected from a living cattle, or the rumen fluid of the butchered livestock, which has been treated as waste, may be used in the present invention.

The collected rumen fluid may be used in its original conditions (as a "raw rumen fluid") without any pre-treatment. The rumen fluid may be stored with freezing and the like and used after storage.

It is preferable to carry out the reaction between the rumen fluid collected from the ruminant and the cellulose-containing waste in anaerobic conditions in order to make the microorganisms sufficiently exert their activities and to increase an efficiency in the production of the organic acids.

The anaerobic conditions may be generated, for example, by co-existence of a compound with the reducing property selected from the group consisting of cysteine, sodium sulfate, ascorbic acid, methionine, thioglycolic acid, DDT and any combination thereof with in a system of the reaction between the rumen fluid collected from a ruminant with the cellulose-containing waste. For example, the cysteine concentration is preferably 0.025~0.25% by weight, more preferably about 0.1% by weight of the whole reaction system, when it is added alone. Alternatively, the reaction between the rumen fluid and the cellulose-containing waste may be carried out in the closed system under atmosphere of nitrogen or hydrogen in order to obtain the anaerobic conditions.

It is preferred to keep the reaction temperature in a range around the temperature in the rumen of the ruminant, for example, preferably at 30° C.~45° C., more preferably at 37° C.~42° C. in the case of the rumen fluid from the cattle.

It is preferable that pH of the reaction is in such a range that the microorganisms can sufficiently exert their activities so as to increase the efficiency in the production of the organic acids, such as for example, in a range of 5.0~8.0, more preferably in a range of 6.0~7.0.

The waste concentration in the reaction system may be optionally controlled depending on its kind, being usually about 1~10% by weight, for example, 0.5%~7% by weight, and preferably 5%~7% by weight of the whole reaction system.

The reaction time between the rumen fluid and the cellulose-containing waste may be optionally controlled by those skilled in the art depending on various reaction conditions such as the kind, amount of the cellulose-containing waste, the condition of the rumen fluid and the like, so that a desired amount of the organic acids can be produced.

The reaction may be carried out with any suitable apparatus or means known for those skilled in the art. For example, a mixture of the rumen fluid and the cellulose-containing waste may be reacted with stirring or shaking in a reaction vessel for a few hours to ten and a few hours, as described in the Examples of the present specification. When the methane fermentation is performed by using the processed rumen fluid obtained as a result of the reaction between the rumen fluid and the cellulose-containing waste, the time for said reaction may be 24 hours or less, preferably about 6 hours.

According to the method of the present invention, acetic acid, which is a main raw material for methane fermentation, can be produced in a few hours at its final concentration of acetic acid of 10 g/L (reaction mixture) or more, preferably 12 g/L (reaction mixture) or more, more preferably 15 g/L (reaction mixture) or more, up to about 18 g/L (reaction mixture). Furthermore, propionic acid and butyric acid will be decomposed into acetic acid in accordance with the following chemical equation, and to serve as the raw material for methane fermentation as well:

[Chemical Equation 1]

$CH_3CH_2CH_2COO^- + 2H_2O \rightleftharpoons 2CH_3COO^- + 2H_2 + H^+ + 48.1$ J/mol $CH_3CH_2COO^- + 3H_2O \rightleftharpoons CH_3COO^- + HCO_3^- + 3H_2 + H^+ + 76.1$ kJ/mol Furthermore, the present invention relates to a method for the production of methane, comprising performing methane fermentation with any method known for those skilled in the art using as the raw material the organic acids or processed rumen fluid containing said organic acids produced by the method according the present invention. Material to be used for the methane fermentation may be any one containing the methane bacteria such as various kinds of sludge that have been generated in various disposing facilities of household or industrial waste products and the like, including, for example, digested sludge produced in an anaerobically-disposing facility for discharged water.

The present invention will be specifically explained with reference to the following examples, which will be provided only for the purpose of explanation of the present invention. Accordingly, they shall not be construed as restricting or limiting a scope of the present invention by any means. Those skilled in the art will readily understand that various embodiments or aspects can be performed based on the technical concepts disclosed in the claims.

EXAMPLES

1. Collection of Raw Rumen Fluid

Rumen fluid was collected orally with a rumen catheter (a tool to obtain stomach fluid of a cow) from a cow about one hour after the cow had been fed, and immediately transferred to and kept in an incubator that had been pre-heated at 37° C.

2. Study on an Amount of the Additive Cysteine (1) Materials

Raw rumen fluid: 300 ml

Waste paper (waste paper typed with "A"~"Z" in black ink: 49 characters×17 lines per page): 3 g (1% w/v)

L-cysteine hydrochloride-hydrate: 0 g (0% w/v)~9 g (3% w/v)

(2) Methods 300 ml of the raw rumen fluid, 3 g of the waste paper and 0 g (0% w/v)~9 g (3% w/v) of L-cysteine hydrochloride-hydrate were added into a reaction vessel (500 ml) equipped with a gas-collecting bag. After culture had been carried out at 37° C. for 72 hours with shaking at 140 rpm, the resulting sample was sterilized by filtration with a membrane filter (0.25 μm) and subjected to HPLC for the determination of organic acids.

(3) Results

The results shown in Tables 1 and 2, and FIG. 1, 2, 4~7 have revealed that the addition of cysteine has increased the production of acetic acid that is accessible to methane bacteria. The cysteine concentration is preferably 0.025~0.25% by weight, more preferably of 0.1% by weight of the whole reaction system. If an amount of the added cysteine is lower than the above range, a sufficient result could not be obtained. If said amount is higher than the above range, it would be undesirable since inhibition would occur due to the resulting low pH and its SH group.

TABLE 1

| Cysteine (%) | Acetic Acid (g/L) | Propionic acid (g/L) | Butyric acid (g/L) |
| --- | --- | --- | --- |
| 0 | 10.021 | 3.499 | 2.308 |
| 0.1 | 11.564 | 4.438 | 2.205 |
| 0.25 | 11.337 | 2.737 | 2.289 |
| 0.5 | 7.400 | 1.441 | 1.575 |
| 1 | 6.588 | 1.507 | 1.859 |
| 2 | 5.580 | 1.304 | 1.398 |
| 3 | 5.256 | 1.208 | 1.354 |

TABLE 2

| Cysteine (%) | Acetic Acid (g/L) | Propionic acid (g/L) | Butyric acid (g/L) |
| --- | --- | --- | --- |
| 0 | 9.667 | 2.286 | 1.56 |
| 0.025 | 10.015 | 2.466 | 1.653 |
| 0.05 | 10.167 | 2.093 | 0.931 |
| 0.1 | 10.971 | 2.201 | 1.036 |
| 0.175 | 10.076 | 1.412 | 0.532 |

Figure 1:
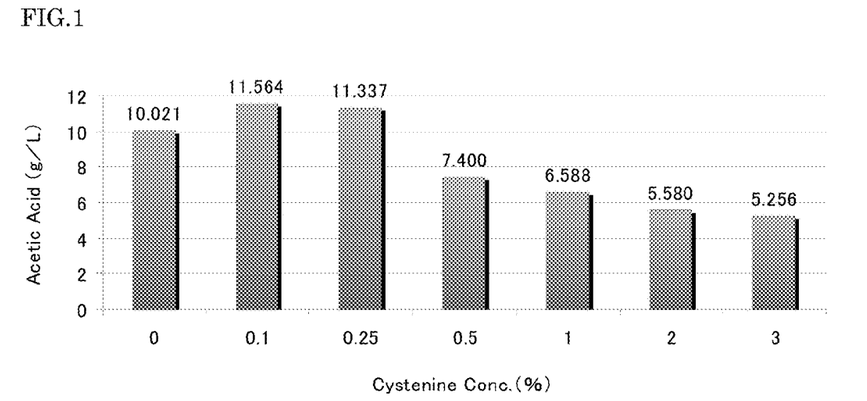
FIG. 1 shows the results of an amount of the production of acetic acid as a function of an amount of additive cysteine in the present method.
Figure 2:
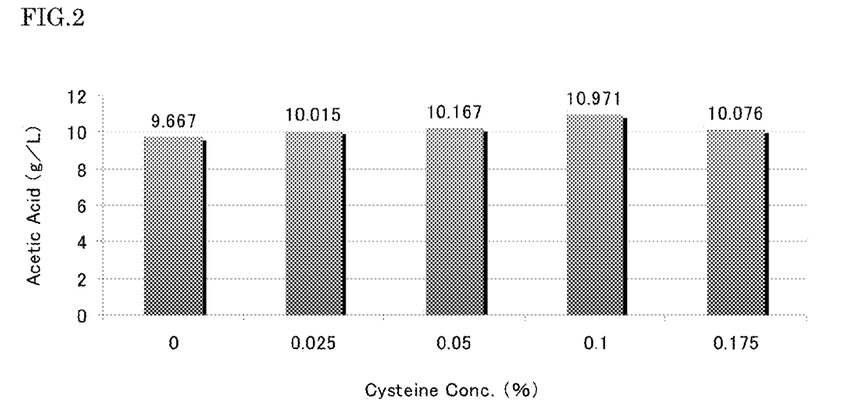
FIG. 2 shows the results of an amount of the production of acetic acid as a function of an amount of additive cysteine in the present method.
Figure 3:
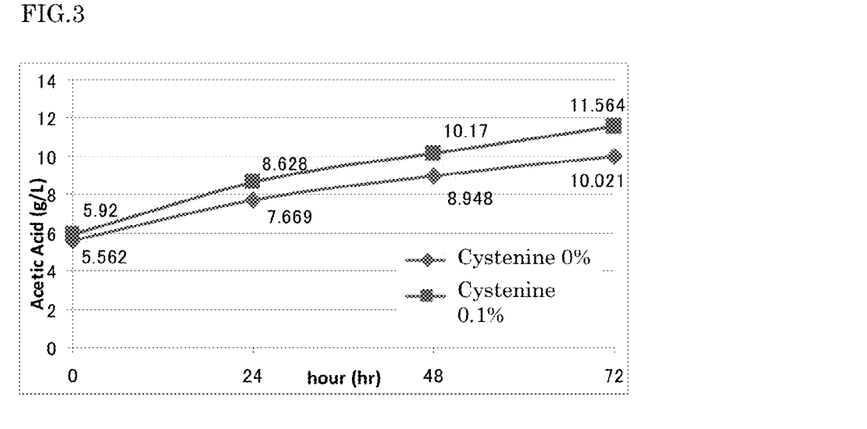
FIG. 3 shows the time course of an amount of the production of acetic acid as a function of an amount of additive cysteine in the present method.
Figure 4:
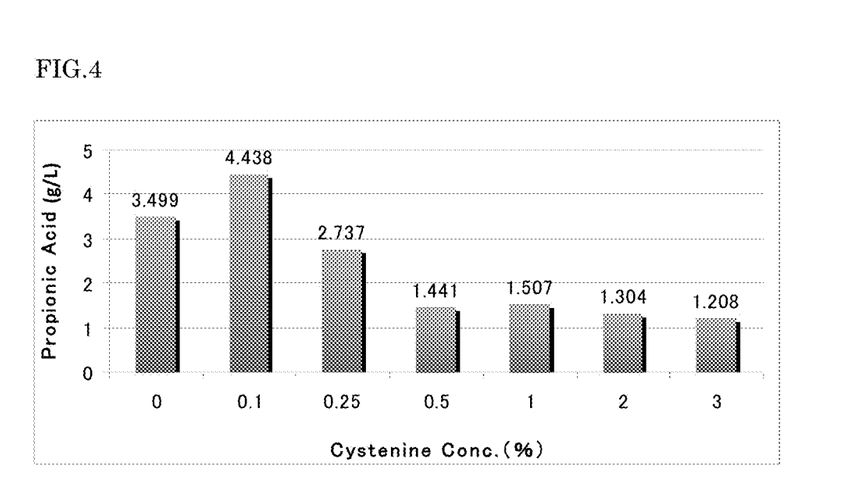
FIG. 4 shows the results of an amount of the production of propionic acid as a function of an amount of additive cysteine in the present method.
Figure 5:
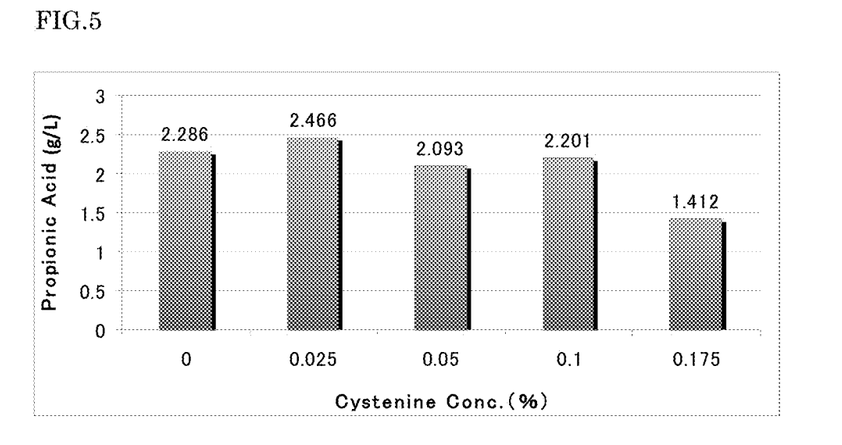
FIG. 5 shows the results of an amount of the production of propionic acid as a function of an amount of additive cysteine in the present method.
Figure 6:
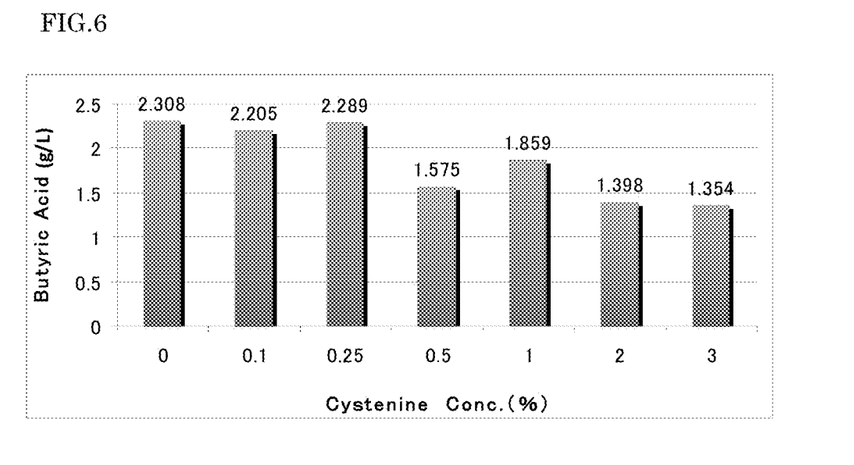
FIG. 6 shows the results of an amount of the production of butyric acid as a function of an amount of additive cysteine in the present method.
Figure 7:
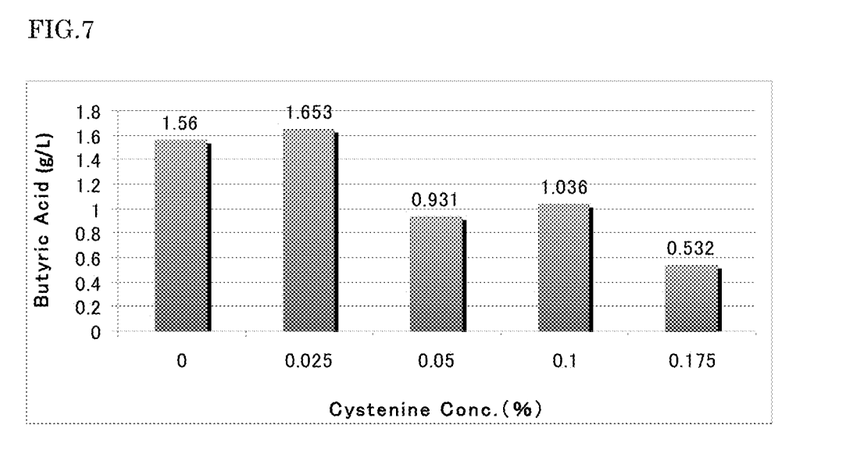
FIG. 7 shows the results of an amount of the production of butyric acid as a function of an amount of additive cysteine in the present method.

The amount of the production of acetic acid was increased by about 1.3 g when compared between the cases of 0% and 0.1% cysteine in the two tests as shown both in Tables 1 and 2, indicating its reproducibility (Table 1: from 10.021 to 11.337 g/L, Table 2: from 9.66 to 10.971 g/L). Accordingly, it was recognized that the addition of 0.1% cysteine was strongly involved in the increase of the amount of the production of acetic acid. Furthermore, it was also confirmed that propionic acid and butyric acid were produced due the addition of cysteine. Also, as shown in the time course of an amount of the production of acetic acid in FIG. 3, it was produced in an amount of 10 g/l after 72 hours in the case of 0% cysteine, but after 48 hours (shortened by 10 hours) in the case of 0.1% cysteine. These results confirmed that the addition of cysteine caused shortening of the reaction time for the production of the raw material for methane fermentation (acceleration of the acid fermentation).

3. Study on Reaction Temperature (1) Materials

Raw rumen fluid: 300 ml

Waste paper (waste paper typed with "A"~"Z" in black ink: 49 characters×17 lines per page): 3 g (1% w/v)

L-cysteine hydrochloride-hydrate: 0.3 g (0.1% w/v)

(2) Methods 300 ml of the raw rumen fluid, 3 g of the waste paper and 0.3 g (0.1% w/v) of L-cysteine hydrochloride-hydrate were added into a reaction vessel (500 ml) equipped with a gas-collecting bag. After culture had been carried out at 37° C., 39.5° C. or 42° C. for 72 hours with shaking at 140 rpm, the resulting sample was sterilized by filtration with a membrane filter (0.25 μm) and subjected to HPLC for the determination of organic acids.

(3) Results

Figure 8:
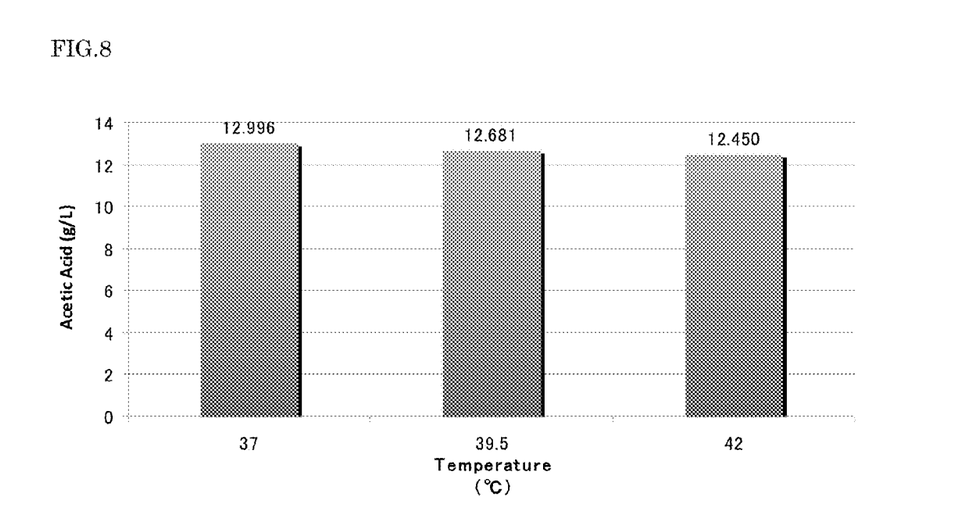
FIG. 8 shows the results of an amount of the production of acetic acid as a function of a reaction temperature in the present method.
Figure 9:
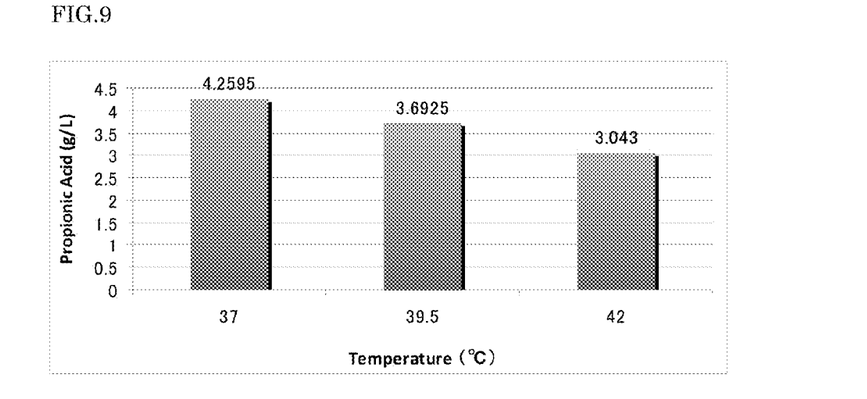
FIG. 9 shows the results of an amount of the production of propionic acid as a function of a reaction temperature in the present method.
Figure 10:
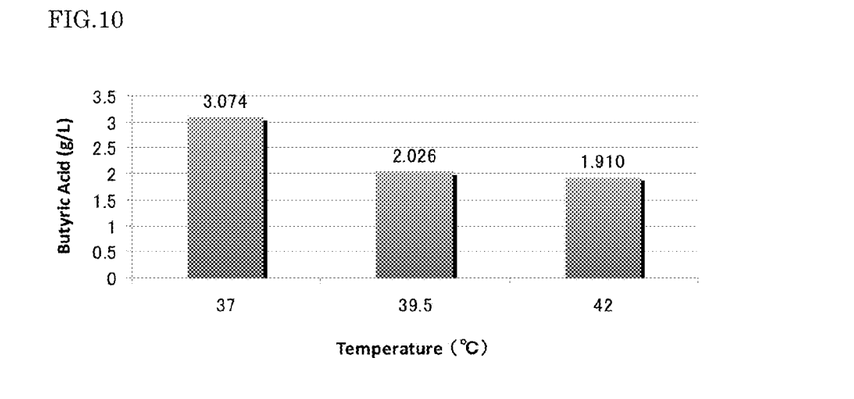
FIG. 10 shows the results of an amount of the production of butyric acid as a function of a reaction temperature in the present method.

The results shown in Table 3, and FIG. 8-10 have first revealed that the waste paper could be solubilized at 37° C., which was lower than the temperature of the cattle (at 38.5° C. in colon and at 39.5° C. in rumen). The reaction temperature is preferably in the range of 37° C.~42° C., more preferably at 37° C. in view of energy for heating. A lower temperature would decrease the activity for decomposing the waste paper, and a higher temperature would also decrease or inactivate the same activity.

TABLE 3

| Temperature (° C.) | Acetic acid (g/L) | Propionic acid (g/L) | Butyric acid (g/L) |
| --- | --- | --- | --- |
| 37 | 12.996 | 4.2595 | 3.074 |
| 39.5 | 12.681 | 3.6925 | 2.026 |
| 42 | 12.450 | 3.043 | 1.910 |

4. Study on the Concentration of the Waste Paper (1) Materials

Raw rumen fluid: 300 ml

Waste paper (waste paper typed with "A"~"Z" in black ink: 49 characters×17 lines per page): 1.5 g (0.5% w/v)~30 g (10% w/v)

L-cysteine hydrochloride-hydrate: 0.3 g (0.1% w/v)

(2) Methods 300 ml of the raw rumen fluid, 1.5 g (0.5% w/v)~30 g (10% w/v) of the waste paper and 0.3 g (0.1% w/v) of L-cysteine hydrochloride-hydrate were added into a reaction vessel (500 ml) equipped with a gas-collecting bag. After culture had been carried out at 37° C. for 72 hours with shaking at 190 rpm, the resulting sample was sterilized by filtration with a membrane filter (0.25 μm) and subjected to HPLC for the determination of organic acids.

(3) Results

Figure 11:
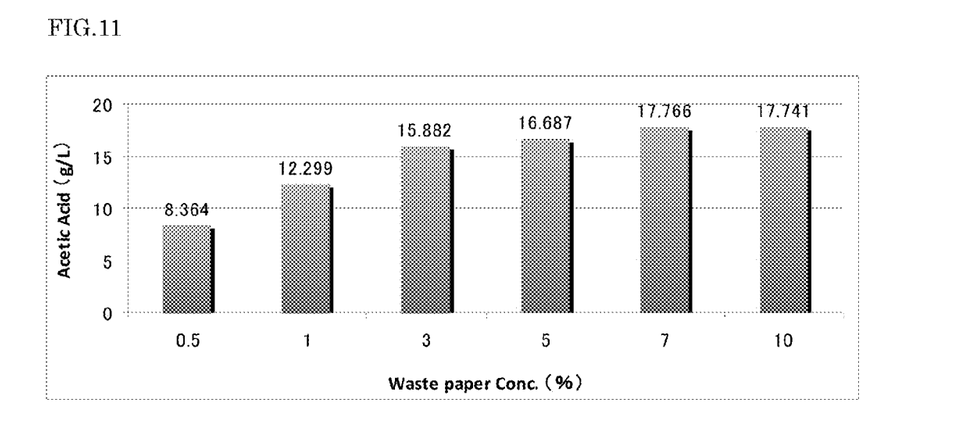
FIG. 11 shows the results of an amount of the production of acetic acid as a function of the concentration of waste paper in the present method.
Figure 12:
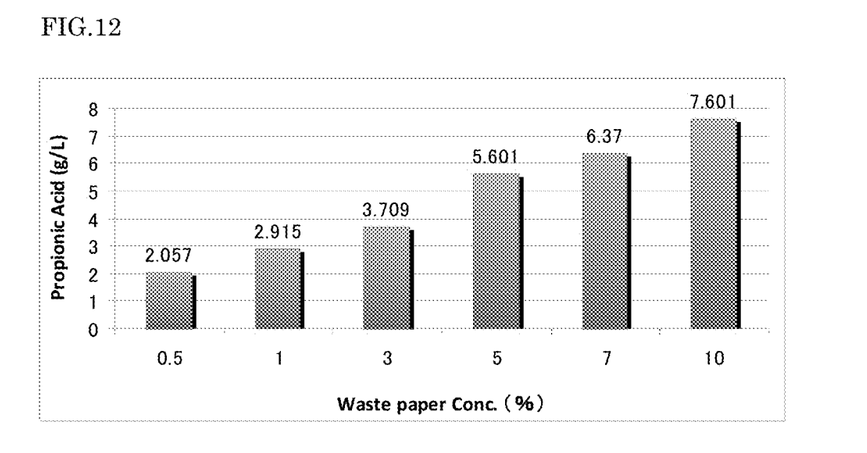
FIG. 12 shows the results of an amount of the production of propionic acid as a function of the concentration of waste paper in the present method.
Figure 13:
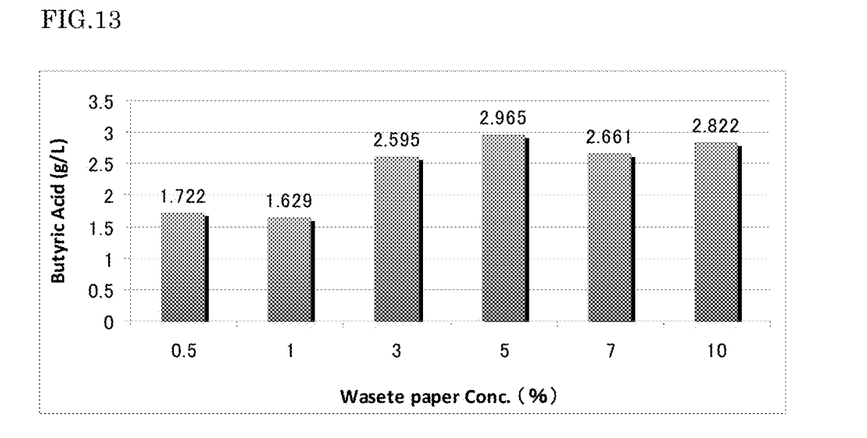
FIG. 13 shows the results of an amount of the production of butyric acid as a function of the concentration of waste paper in the present method.

According to the results shown in Table 4, FIG. 11~13, the concentration of the waste paper is preferably 0. 5%~7% by weight, and more preferably 5%~7% by weight of the whole reaction system. A lower concentration would be inefficient due to a low amount of the organic compounds per unit area, and a higher concentration would cause insufficient solubilization of the waste paper.

TABLE 4

| Concentration of waste paper (%) | Acetic acid (g/L) | Propionic acid (g/L) | Butyric acid (g/L) |
| --- | --- | --- | --- |
| 0.5 | 8.364 | 2.057 | 1.722 |
| 1 | 12.299 | 2.915 | 1.629 |
| 3 | 15.882 | 3.709 | 2.595 |
| 5 | 16.687 | 5.601 | 2.965 |
| 7 | 17.766 | 6.37 | 2.661 |
| 10 | 17.741 | 7.601 | 2.822 |

5. Evaluation Method

The evaluation was made in terms of the concentration of acetic acid that was most accessible to the methane bacteria. The organic acids were determined with the HPLC by means of a post-column method using a BTB agent. The conditions for the determination are as follows:

Pump: PU-980(JASCO)

Detector: 870-UV

Wave length: 445 nm

Column:RSpak HC-G, RSpak KC-811(Shodex)

Flow rate: 0.8 ml/min

Temperature: 60° C. (column), 20° C. (room temperature)

Reagent Pump: PU-980(JASCO)

Regent floe rate: 1.2 ml/min

6. Methane Fermentation of the Processed Rumen Fluid (1) Materials

1) Preparation of the processed rumen fluid

Raw rumen fluid: 300 ml (collected as above)

Waste paper (waste paper typed with "A"~"Z" in black ink: 49 characters×17 lines per page): 3 g (1% w/v)

L-cysteine hydrochloride-hydrate: 0.3 g (0.1% w/v)

2) Preparation of Seed Sludge for Methane Fermentation

The substrate and nutrient salts shown in Table 5 were added to 2 L of the digested sludge produced in an anaerobically-disposing facility of discharged water, and cultured for one month to give seed sludge.

TABLE 5

| $CH_3COONa$ | 2 g/L |
| --- | --- |
| Waste paper | 2 g/L |
| $NH_4Cl$ | 2 g/L |
| $KH_2PO_4$ | 0.016 g/L |
| $CaCl_2 \cdot 2H_2O$ | 0.025 g/L |
| $MgCl_2 \cdot 6H_2O$ | 0.025 g/L |
| Fe-EDTA | 0.03 g/L |
| $CoCl_2 \cdot 6H_2O$ | 0.005 g/L |
| $MnCl_2 \cdot 4H_2O$ | 0.005 g/L |
| Yeast extract | 0.1 g/L |
| $NiCl_2 \cdot 6H_2O$ | 0.005 g/L |

(2) Methods 300 ml of the raw rumen fluid, 3 g (1% w/v) of the waste paper and 0.3 g (0.1% w/v) of L-cysteine hydrochloride-hydrate were added into a reaction vessel (500 ml) equipped with a gas-collecting bag. After culture had been carried out at 37° C. for 6 or 24 hours with shaking at 140 rpm. The processed rumen fluid thus obtained was added to 600 mL of the seed sludge at a ratio of 30 mL/day (HRT20 days) to carry out methane fermentation at 35° C., 150 rpm for 20 days. The generated biogas was subjected to gas chromatography to determine a gas composition. In the control, 0.3 g of the waste paper and 30 mL of distilled water were added without the treatment by rumen in the same way.

(3) Results

Figure 14:
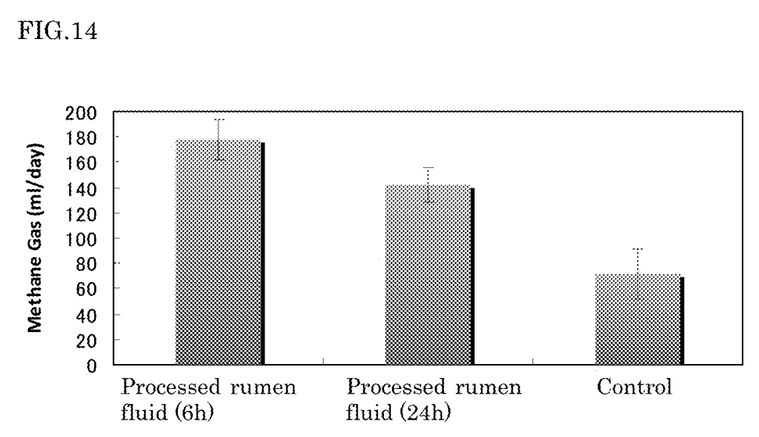
FIG. 14 shows an average of an amount of the generated methane gas per day in the methane fermentation according to the present method.

FIG. 14 shows an average of an amount of the generated methane gas per day. It indicates that the highest mount (177.7 mL/day with a standard deviation of 16.1 mL/day) of the generated methane gas was shown by the addition of the processed rumen fluid obtained for 6-hour treatment with the rumen fluid, followed by the amount (142.0 mL/day with a standard deviation of 13.4 mL/day) for the processed rumen fluid obtained by 24-hour treatment with the rumen fluid and the amount (71.7 mL/day with a standard deviation of 19.6 mL/day) by the control.

Furthermore, an amount of the generated methane gas by the processed rumen fluid of 300 mL volume (14 mL for 6 hours, 147 mL for 24 hours) was converted into that generated by an input in a day (30 mL), and summed up with the amount the methane gas that has generated in the methane fermentation to give methane yield (Table 6). The theoretical value used in the calculation of the yield (%) was obtained based on COD of the waste paper and the rumen fluid (Table 7: rumen fluid treatment, Table 8: Control)

TABLE 6

| | Amount of the generated methane gas | | | | |
|---|---|---|---|---|---|
| | Treatment with rumen fluid (ml) | Methane fermentation (ml) | Methane gas Total (ml) | Theoretical Value (ml) | Yield (%) |
| Processed rumen fluid (6 h) | 1.4 | 177.7 | 179.1 | 213.5 | 83.9 |
| Processed rumen fluid (24 h) | 14.7 | 142.0 | 156.7 | 213.5 | 73.4 |
| Control | 0 | 71.7 | 71.7 | 108.5 | 66.1 |

TABLE 7

| | COD (g) | COD (Total of the raw material) | coefficient | Theoretical value (ml) |
|---|---|---|---|---|
| Waste paper (0.3 g) | 0.31 | 0.61 | 350 | 213.5 |
| Rumen fluid (30 ml) | 0.3 | | | |

TABLE 8

| | COD (g) | coefficient | Theoretical value (ml) |
|---|---|---|---|
| Waste paper (0.3 g) | 0.31 | 350 | 108.5 |

Provided that $CH_4 + 2O_2 \rightarrow CO_2 + 2H_2O$ and that oxygen (64 g) corresponds to COD of methane (22.4 L), the following equation is obtained:

COD 1 g=$CH_4$ 0.35 L (=22.4÷64)=$CH_4$ 350 ml.

Table 6 shows that the methane yield was increased in the order of the processed rumen fluid (6 h) >the processed rumen fluid (24 h) >the control, confirming the effectiveness of the treatment with the rumen fluid. Furthermore, it was difficult to continue the methane fermentation in the control as long as ammonium carbonate had been regularly added as a nitrogen source (data not shown). On the other hand, as the processed rumen fluid contained soluble nitrogen of 300-400 mg/L, it was not necessary to externally add any nitrogen source. Accordingly, it was demonstrated that the rumen fluid was effective not only as a catalyst for solubilizing the waste paper but also as the nitrogen source.

Although the processed rumen fluid (24 h) produced a larger amount of acetic acid since the waste paper was sufficiently solubilized, an amount of the generated $CO_2$ during the treatment with the rumen fluid was about 20 times higher than that produced by the processed rumen fluid (6 h). As a result, loss of carbon resource (carbon originated from the waste paper) as $CO_2$ was large, and there was a tendency that the amount of the generated methane gas by the addition of the processed rumen fluid (24 h) was lower than that by the processed rumen fluid (6 h). Thus, it is considered that the reaction time may be 24 hours or less, preferably about 6 hours.

INDUSTRIAL APPLICABILITY

According to the present invention, it is possible to produce organic acids to serve as the raw material for methane fermentation from the cellulose-containing waste such as waste paper, and to produce methane gas by methane fermentation using as the raw material the organic acids thus produced. The present invention may be therefore utilized finally in the fields of industry for the production of fuel gas, electricity and the like.

What is claimed:

1. A method for increasing the amount of acetic acid during the production of organic acids to serve as the raw material for methane fermentation comprising:
   combining isolated rumen fluid collected from a ruminant with cellulose-containing waste and cysteine to form a reaction mixture; and
   producing acetic acid from said reaction mixture under anaerobic conditions,
   wherein said cysteine is present at a concentration of 0.1-0.25% by weight of the whole reaction mixture,
   wherein said rumen fluid comprises a microorganism that produces acetic acid, and
   wherein the production of acetic acid is increased relative to the production of acetic acid from a reaction mixture without said cysteine.

2. The method according to claim 1, wherein the cellulose-containing waste is waste paper.

3. The method according to claim 1, wherein the ruminant is cattle.

4. The method according to claim 1, wherein the reaction between the rumen fluid with the cellulose-containing waste is carried out in a closed system under atmosphere of nitrogen or hydrogen.

5. The method according to claim 1, wherein the reaction is kept at 30° C.-45° C.

6. The method according to claim 1, wherein pH of the reaction is in a range of 5.0-8.0.

7. The method according to claim 1, wherein a waste concentration in the reaction system is 0.5%-7% by weight.

8. The method according to claim 1, wherein a final concentration of generated acetic acid is 10 g/L (reaction mixture) or more.

9. The method according to claim 2, wherein the ruminant is cattle.

10. The method according to claim 4, wherein the reaction is kept at 30° C.-45° C.

11. The method according to claim 4, wherein pH of the reaction is in a range of 5.0-8.0.

12. The method according to claim 5, wherein pH of the reaction is in a range of 5.0-8.0.

13. The method according to claim 4, wherein a waste concentration in the reaction system is 0.5%-7% by weight.

14. The method according to claim 5, wherein a waste concentration in the reaction system is 0.5%-7% by weight.

15. The method according to claim 6, wherein a waste concentration in the reaction system is 0.5%-7% by weight.

16. The method according to claim 4, wherein a final concentration of generated acetic acid is 10 g/L or more.

17. The method according to claim 5, wherein a final concentration of generated acetic acid is 10 g/L or more.

18. The method according to claim 6, wherein a final concentration of generated acetic acid is 10 g/L or more.

19. The method according to claim 1, wherein pH of the reaction is in a range of 6.0-7.0.

20. The method according to claim 4, wherein pH of the reaction is in a range of 6.0-7.0.

21. The method according to claim 1, wherein the reaction conditions allow for the production of acetic acid to be selectively increased relative to propionic acid or butyric acid.

\* \* \* \* \*